(12) United States Patent
Ikeda et al.

(10) Patent No.: US 11,364,181 B2
(45) Date of Patent: Jun. 21, 2022

(54) INORGANIC-ORGANIC COMPOSITE MEDICAL MATERIAL AND METHOD FOR PRODUCING INORGANIC-ORGANIC COMPOSITE MEDICAL MATERIAL

(71) Applicant: SUN MEDICAL CO., LTD., Shiga (JP)

(72) Inventors: Hiroshi Ikeda, Kitakyusyu (JP); Hiroshi Shimizu, Fukuoka (JP); Hideyuki Ueki, Moriyama (JP)

(73) Assignee: SUN MEDICAL CO., LTD., Shiga (JP)

( * ) Notice: Subject to any disclaimer, the term of this patent is extended or adjusted under 35 U.S.C. 154(b) by 128 days.

(21) Appl. No.: 16/614,679

(22) PCT Filed: May 18, 2018

(86) PCT No.: PCT/JP2018/019282
§ 371 (c)(1),
(2) Date: Nov. 18, 2019

(87) PCT Pub. No.: WO2018/212321
PCT Pub. Date: Nov. 22, 2018

(65) Prior Publication Data
US 2020/0179239 A1 Jun. 11, 2020

(30) Foreign Application Priority Data

May 19, 2017 (JP) .............................. JP2017-100146

(51) Int. Cl.
*A61K 6/887* (2020.01)
*A61C 5/70* (2017.01)
(Continued)

(52) U.S. Cl.
CPC ................ *A61K 6/887* (2020.01); *A61C 5/70* (2017.02); *A61K 6/15* (2020.01); *A61K 6/802* (2020.01); *A61K 6/84* (2020.01)

(58) Field of Classification Search
CPC .................................................... A61K 6/887
See application file for complete search history.

(56) References Cited

U.S. PATENT DOCUMENTS 4,481,036 A 11/1984 Panzera
4,764,497 A * 8/1988 Yuasa ...................... A61K 6/17
502/235

(Continued)

FOREIGN PATENT DOCUMENTS

EP 393525 A2 10/1990
JP S59-195551 A 11/1984
(Continued)

OTHER PUBLICATIONS

Ikeda, H.; Fujino, S.; Kajiwara, T. J. Ceram. Soc. Japan 2011, 119, 65-69 (Year: 2011).*

(Continued)

*Primary Examiner* — Michael F Pepitone
(74) *Attorney, Agent, or Firm* — Rankin, Hill & Clark LLP

(57) ABSTRACT

An inorganic-organic composite medical material includes a two-phase co-continuous structure of an inorganic substance having open pores and an organic polymer filling the open pores, wherein the open pores have an average pore diameter of 1 nm or more and 100 nm or less, and the inorganic substance has a specific surface area of 100 $m^2/g$ or less.

7 Claims, 7 Drawing Sheets

(51) Int. Cl.
*A61K 6/802* (2020.01)
*A61K 6/84* (2020.01)
*A61K 6/15* (2020.01)

(56) References Cited

U.S. PATENT DOCUMENTS

| | | | |
|---|---|---|---|
| 5,750,258 A * | 5/1998 | Sakai | C08K 9/06 |
| | | | 428/405 |
| 5,843,348 A | 12/1998 | Giordano | |
| 5,852,096 A * | 12/1998 | Heindl | C09C 1/3081 |
| | | | 524/492 |
| 8,507,578 B2 | 8/2013 | Sadoun | |
| 2012/0107589 A1* | 5/2012 | Fujino | C03C 3/06 |
| | | | 428/219 |
| 2015/0316515 A1* | 11/2015 | Lauber | B01D 15/305 |
| | | | 73/61.55 |

FOREIGN PATENT DOCUMENTS

| | | | |
|---|---|---|---|
| JP | S63-252981 A | 10/1988 | |
| JP | H02-275787 A | 11/1990 | |
| JP | H05-319959 A | 12/1993 | |
| JP | H07-161453 A | 6/1995 | |
| JP | H09-098990 A | 4/1997 | |
| JP | H10-043209 A | 2/1998 | |
| JP | 2001-279106 A2 | 10/2001 | |
| JP | 5276175 | 8/2013 | |
| KR | 2015-0070714 A | 6/2015 | |
| WO | 2011/004852 A1 | 1/2011 | |

OTHER PUBLICATIONS

International Preliminary Report on Patentability dated Nov. 19, 2019 issued for PCT/JP2018/019282, total 13 pages.
Wei et al., "Synthesis of Polymer-Mesoporous Silica Nanocomposites", Materials, 2010, 3, pp. 4066-4079; Cited in Japanese Office Action dated May 11, 2021 issued in the corresponding Japanese Patent Application No. 2019-518885.
International Search Report (ISR) dated Aug. 7, 2018 filed in PCT/JP2018/019282.
Ikeda H. et al., Development of Mesoporous Silica Using Sintering of Nanosilica, IEICE Technical Report, 2016, vol. 116, No. 169, pp. 1-2 with its English translation.; Cited in ISR.
Indraneil Mukherjee et la., Monomer Templated Mesoporous Materials for Dental Applications, PMSE Preprints, 2008, vol. 99, pp. 520-521.; Cited in ISR.
Frederik Kotz et al., Three-dimensional printing of transparent fused silica glass, Nature, 2017, vol. 544, total 6 pages.

* cited by examiner

INORGANIC-ORGANIC COMPOSITE MEDICAL MATERIAL AND METHOD FOR PRODUCING INORGANIC-ORGANIC COMPOSITE MEDICAL MATERIAL

CROSS-REFERENCE TO RELATED APPLICATIONS

This application is a National Phase Application of International Application No. PCT/JP2018/019282, filed May 18, 2018, which claims the priority of Japan Patent Application No. 2017-100146, filed May 19, 2017. The present application claims priority from both applications and each of these applications is herein incorporated in their entirety by reference.

TECHNICAL FIELD

The present invention relates to an inorganic-organic composite medical material, and a method for producing an inorganic-organic composite medical material.

BACKGROUND ART

In the medical field, it has been known to replace forms and functions of missing parts of the human body with an artificial product (prosthesis). For example, in dental treatments, dental materials are used to restore the crown decayed by, for example, caries. For such a dental material, a composite material of inorganic material and organic material has been examined to ensure required mechanical properties.

For example, Patent Document 1 has proposed a dental filler including a ceramics network material, and a cured product of a monomer injected into the ceramics network material (for example, see Patent Document 1).

Such a dental filler is produced as follows: ceramics particles having a particle size of 0.1 μm to 10 μm are dispersed in a medium to prepare a suspension, and then the suspension is dried, and then the dried suspension is sintered at 1000° C. to 1400° C. to form a sintered ceramics network material, and then a monomer is injected into the ceramics network material and cured.

CITATION LIST

Patent Document

Patent Document 1: Japanese Unexamined Patent Publication No. H9-98990

SUMMARY OF THE INVENTION

Problem to be Solved by the Invention

However, the dental material that restores the crown makes contact with enamels (natural human enamel) of the opposing tooth in occlusion. At this time, when the hardness of the dental material is smaller than enamel, the dental material is worn (attrition), and when the hardness of the dental material is larger than that of enamel, enamels of the opposing tooth is worn (attrition). Therefore, the hardness of the dental material of about the same as that of the enamel is desired.

However, the hardness of the dental filler described in Patent Document 1 is significantly smaller than the hardness of enamel, and it is difficult to improve the hardness of the dental filler to about the same as that of enamel.

As a result, with the dental filler described in Patent Document 1, the wear (attrition) in occlusion cannot be suppressed. In various medical fields as well, an inorganic-organic composite material having a suitable hardness as a prosthetic has been desired.

Thus, the present invention provides an inorganic-organic composite medical material having a suitable hardness as a prosthetic, and a method for producing an inorganic-organic composite medical material.

Means for Solving the Problem

The present invention [1] includes an inorganic-organic composite medical material having a two-phase co-continuous structure of an inorganic substance having open pores and an organic polymer filling the open pores, wherein the open pores have an average pore diameter of 1 nm or more and 100 nm or less, and the inorganic substance has a specific surface area of 100 $m^2$/g or less.

However, when the open pore has an average pore diameter of less than the above-described lower limit, the open pores cannot be sufficiently filled with the organic polymer, and the two-phase co-continuous structure of inorganic substance and organic polymer may not be ensured. In this case, vacant spaces are caused in the inorganic substance, and therefore the inorganic-organic composite medical material may be brittle.

Furthermore, with the dental filler described in Patent Document 1, the average pore diameter of the open pores is more than the above-described upper limit. When the open pores have the average pore diameter of more than the above-described upper limit, although the two-phase co-continuous structure of inorganic substance and organic polymer can be ensured, improvement in the hardness of the inorganic-organic composite medical material is limited. Furthermore, even when the open pore has the average pore diameter of the above-described upper limit or less, with the inorganic substance having the specific surface area of more than the above-described upper limit, improvement in the hardness of the inorganic-organic composite medical material cannot be achieved sufficiently.

With the above-described configuration, the open pore has the average pore diameter of the above-described lower limit or more, and therefore the open pores of the inorganic substance can be sufficiently filled with the organic polymer, and the two-phase co-continuous structure of inorganic substance and organic polymer can be ensured. Therefore, the inorganic-organic composite medical material can be suppressed from being brittle.

Furthermore, the open pore has the average pore diameter of the above-described upper limit or less, and the inorganic substance has the specific surface area of the above-described upper limit or less, and therefore the hardness of the inorganic-organic composite medical material can be improved.

As a result, hardness of the inorganic-organic composite medical material can be a suitable hardness for prosthetics, particularly about the same as the hardness of enamel.

The present invention [2] includes the inorganic-organic composite medical material described in [1] above, wherein the inorganic substance is metal oxide.

With such a configuration, the inorganic substance is metal oxide, and therefore hardness of the inorganic-organic composite medical material can be reliably improved to a suitable hardness as prosthetics, particularly, to about the hardness of enamel.

The present invention [3] includes the inorganic-organic composite medical material described in [1] or [2] above, wherein the organic polymer is a polymer of an ingredient monomer having an ethylenic unsaturated double bond.

With such a configuration, the organic polymer is a polymer of an ingredient monomer having an ethylenic unsaturated double bond, and therefore the open pores can be filled with the organic polymer reliably, and the two-phase co-continuous structure of inorganic substance and organic polymer can be stably ensured.

The present invention [4] includes a method for producing an inorganic-organic composite medical material, the method including the steps of: dispersing inorganic nanoparticles in a dispersion medium; drying the dispersion medium to form a porous precursor having nanopores from the inorganic nanoparticles; calcining the porous precursor to form an inorganic calcined substance having open pores with an average pore diameter of 1 nm or more and 100 nm or less and having a specific surface area of 100 $m^2/g$ or less; and filling the open pores of the inorganic calcined substance with an organic polymer, thereby producing an inorganic-organic composite medical material having a two-phase co-continuous structure of the inorganic substance having open pores and the organic polymer filling the open pores.

With this method, the inorganic nanoparticles are dispersed in a dispersion medium, and then the dispersion medium is dried to form a porous precursor having nanopores, and then the porous precursor is calcined to form an inorganic calcined substance having open pores with an average pore diameter of within the range of the above-described nano-order, and having a specific surface area of the above-described upper limit or less, and then the open pores of the inorganic calcined substance are filled with the organic polymer. In this manner, the inorganic-organic composite medical material having a suitable hardness as prosthetics can be produced.

However, the hardness of teeth enamel changes depending on the age of the patient or the part of the teeth, and the stress such as occlusion applied to the crown changes depending on the patient. Therefore, the inorganic-organic composite medical material having a hardness suitable for patients is desired.

With the above-described method, the porous precursor is calcined to form the inorganic calcined substance having open pores, and therefore by suitably changing the conditions for calcining, the average pore diameter of the open pore can be adjusted to be in the range of the above-described nano-order, and the specific surface area of the inorganic calcined substance can be adjusted to the above-described upper limit or less. Hardness of the inorganic-organic composite medical material changes depending on the conditions of the inorganic calcined substance, such as the average pore diameter of the open pores and the specific surface area.

Therefore, with an easy method, by adjusting the average pore diameter of the open pore within the above-described range, and adjusting the specific surface area to the above-described upper limit or less, hardness of the inorganic-organic composite medical material can be adjusted, and the inorganic-organic composite medical material with desired hardness can be produced efficiently.

The present invention [5] includes the method for producing an inorganic-organic composite medical material described in [4] above, wherein in the step of dispersing the inorganic nanoparticles in the dispersion medium, a water-soluble polymer is blended in the dispersion medium along with the inorganic nanoparticles to disperse the inorganic nanoparticles in the dispersion medium, and in the step of forming the porous precursor, the dispersion medium is dried to form the porous precursor having nanopores based on the water-soluble polymer from the inorganic nanoparticles and the water-soluble polymer.

With this method, the water-soluble polymer is blended in the dispersion medium along with the inorganic nanoparticles to disperse the inorganic nanoparticles, and then the dispersion medium is dried to form the porous precursor. Therefore, in the porous precursor, nanopores based on the water-soluble polymer can be reliably formed.

Then, by calcining the porous precursor having nanopores, the inorganic calcined substance is formed, and therefore the open pores having an average pore diameter of the above-described nano-order range can be reliably formed.

The present invention [6] includes the method for producing an inorganic-organic composite medical material described in [4] or [5] above, wherein in the step of forming the inorganic calcined substance, the porous precursor is calcined under milder conditions than the conditions where the inorganic calcined substance is formed into a compact inorganic calcined substance having no open pore.

With this method, the porous precursor is calcined under milder conditions than the conditions where the inorganic calcined substance is formed into a compact inorganic calcined substance having no open pore, and therefore open pores can be reliably formed in the inorganic calcined substance.

The present invention [7] includes the method for producing an inorganic-organic composite medical material described in [6] above, wherein the average pore diameter of the open pores is adjusted to be in the range of 1 nm or more and 100 nm or less by the milder conditions.

With this method, the porous precursor is calcined under milder conditions, and the average pore diameter of the open pore is adjusted to be in the range of the above-described nano-order, and therefore hardness of the inorganic-organic composite medical material can be reliably adjusted.

The present invention [8] includes the method for producing an inorganic-organic composite medical material described in any one of the above-described [4] to [7], wherein the step of filling the open pores of the inorganic calcined substance with the organic polymer includes introducing an ingredient monomer of the organic polymer in the open pores and polymerizing the ingredient monomer introduced in the open pores to form the organic polymer.

With this method, the ingredient monomer of the organic polymer is introduced into the open pore, and then the ingredient monomer is polymerized to form an organic polymer, and therefore compared with the case where the polymerized organic polymer is introduced into the open pores, the ingredient monomer can be smoothly introduced into the open pores, and also the open pores can be reliably filled with the organic polymer.

Effects of the Invention

With the inorganic-organic composite medical material of the present invention, hardness of the inorganic-organic composite medical material can be set to a suitable hardness as prosthetics, particularly, about the hardness of enamel.

With the method for producing an inorganic-organic composite medical material of the present invention, with an easy method, hardness of the inorganic-organic composite medical material can be adjusted, and the inorganic-organic composite medical material with desired hardness can be produced efficiently.

DESCRIPTION OF THE EMBODIMENTS

<Inorganic-Organic Composite Medical Material>

Figure 1:
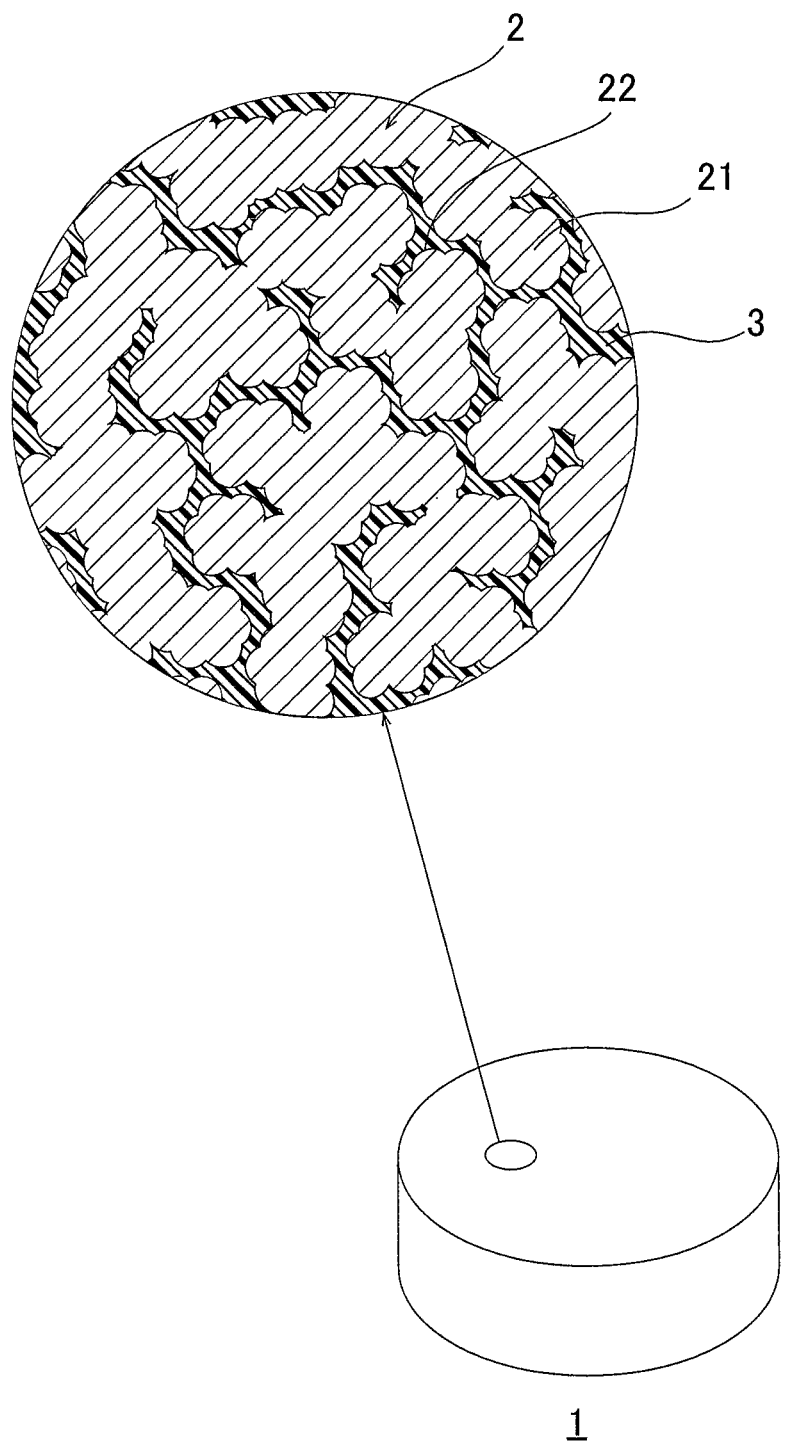
FIG. 1 shows a schematic transverse section of nanocomposite resin as an embodiment of the inorganic-organic composite medical material of the present invention.

With reference to FIG. 1, a nanocomposite resin 1 as an embodiment of the inorganic-organic composite medical material of the present invention is described.

The nanocomposite resin 1 has a two-phase co-continuous structure of an inorganic substance 2 having open pores (communicating pores) 22 and an organic polymer 3 filling the open pores 22. In the nanocomposite resin 1, the inorganic substance 2 and the organic polymer 3 are three-dimensionally continuous. The inorganic substance 2 and the organic polymer 3 can be phase separated from each other, or can be chemically bonded to each other by grafting process. In FIG. 1, the nanocomposite resin 1 has, for convenience, a cylindrical shape, but the shape of the nanocomposite resin 1 is not particularly limited.

(1) Inorganic Substance

The inorganic substance 2 is porous substance having a monolith structure, and includes a skeleton 21 of a continuous three-dimensional network and open pores 22 defined by the skeleton 21.

The material of the inorganic substance 2 is not particularly limited, and a known inorganic substance used for medical materials is used. For the material of the inorganic substance 2, for example, metal materials and non-metal materials (ceramics) are used.

For the metal material, for example, gold, silver, platinum, palladium, cobalt, chromium, titanium, aluminum, iron, and alloys thereof are used.

For the non-metal material (ceramics), for example, metal oxide, carbide, nitride, phosphate, sulfate, and fluoride are used.

Metal oxides include single metal oxide including only one element from metal elements (for example, Al, Ti, Zr, etc.) and semi-metal elements (for example, Si, B, Ge, etc.), and composite metal oxides including two or more elements from the metal elements and semi-metal elements.

For the single metal oxide, for example, silica ($SiO_2$), titania ($TiO_2$), alumina ($Al_2O_3$), and zirconia ($ZrO_2$) are used. For the composite metal oxide, for example, silica-zirconia, silica-titania, silica-alumina, and alumina-zirconia are used.

For the carbide, for example, silicon carbide is used. For the nitride, for example, silicon nitride is used. For the phosphate, for example, calcium phosphate and hydroxyapatite are used. For the sulfate, for example, barium sulfate is used. For the fluoride, for example, calcium fluoride, ytterbium fluoride, and yttrium fluoride are used.

These materials of the inorganic substance 2 can be used singly, or can be used in combination of two or more.

The inorganic substance 2 can be monocrystalline, polycrystalline, or noncrystalline, preferably, it is polycrystalline or noncrystalline.

For the polycrystal inorganic substance 2, for example, polycrystal metal oxides (single metal oxide and composite metal oxide), to be specific, polycrystal silica, polycrystal titania, polycrystal alumina, polycrystal zirconia, and polycrystal silica-zirconia are used.

Examples of the noncrystal inorganic substance 2 include metal oxide (single metal oxide and composite metal oxide) glass, and to be specific, silica glass (quartz glass), soda-lime-silica glass (for example, $SiO_2$—$Al_2O_3$—$CaO$—$Na_2O$, etc.), borosilicate glass (for example, $SiO_2$—$Al_2O_3$—$B_2O_3$—$Na_2O$, etc.), barium glass (for example, $SiO_2$—$Al_2O_3$—$BaO$—$B_2O_3$, etc.), strontium glass (for example, $SiO_2$—$Al_2O_3$—$SrO$—$B_2O_3$, etc.), lanthanum glass (for example, $SiO_2$—$Al_2O_3$—$ZrO_2$—$P_2O_5$—$La_2O_3$—$Li_2O$—$K_2O$, etc.), aluminnofluorosilicate glass (for example. $SiO_2$—$Al_2O_3$—F—$CaO$—$P_2O_5$—$Na_2O$, etc.), E glass, and C glass are used.

These examples of the inorganic substance 2 include a sintered substance, in which particles of the plurality of inorganic substances 2 are bonded together by calcination. The inorganic substance 2 is preferably sintered inorganic substance 2.

Of these examples of the inorganic substance 2, preferably, an inorganic substance (inorganic substance formed from non-metal material) of non-metal material, more preferably, an inorganic substance (inorganic substance formed from metal oxide) of metal oxide, even more preferably, polycrystal metal oxide, glass metal oxide, particularly preferably, sintered polycrystal metal oxide and sintered glass metal oxide, most preferably, a sintered silica glass is used.

The open pores 22 are a space portion in the inorganic substance 2 excluding the skeleton 21. The open pores 22 are formed by a plurality of air gap communicating each other in a three-dimensional network, and extend throughout the inorganic substance 2. The open pores 22 are open at the surface of the inorganic substance 2 so as to communicate with the outer space of the inorganic substance 2.

The open pores 22 have a nano-order pore diameter. The pore diameter is a cross sectional diameter of a direction orthogonal to the direction of extension of the open pores 22. The open pores 22 have a pore diameter range (pore size distribution) of, for example, 0.5 nm or more, preferably 1 nm or more, and for example, 100 nm or less, preferably 50 nm or less, more preferably 30 nm or less.

The open pores 22 have an average pore diameter of 1 nm or more, preferably 5 nm or more, more preferably 10 nm or more, 100 nm or less, preferably 50 nm or less, even more preferably 30 nm or less, particularly preferably 20 nm or less. The pore size distribution and average pore diameter of the open pores 22 can be calculated by analyzing the measurement results in nitrogen gas adsorption with BJH (Barrett-Joyner-Halenda) method.

When the open pores 22 have an average pore diameter of the above-described lower limit or more, the open pores 22 can be reliably filled with the organic polymer 3, and the two-phase co-continuous structure of the inorganic substance 2 and the organic polymer 3 can be reliably ensured. When the open pores 22 have an average pore diameter of the above-described upper limit or less, hardness of the nanocomposite resin 1 can be improved.

The volume of the open pores 22 in the inorganic substance 2 is, per unit mass of the inorganic substance 2, for example, 0.01 $cm^3/g$ or more, preferably 0.05 $cm^3/g$ or more, more preferably 0.10 $cm^3/g$ or more, and for example, 1.00 $cm^3/g$ or less, preferably 0.40 $cm^3/g$ or less, more preferably 0.20 $cm^3/g$ or less. The volume of the open pores 22 can be calculated by analyzing the measurement result of nitrogen gas adsorption by BJH method.

When the volume of the open pores 22 is within the above-described range, the average pore diameter of the open pores 22 can be set reliably in the above-described range.

The inorganic substance 2 has a specific surface area per unit mass of the inorganic substance 2 of, for example, 0.1 $m^2/g$ or more, preferably 1 $m^2/g$ or more, more preferably 10 $m^2/g$ or more, 100 $m^2/g$ or less, preferably 50 $m^2/g$ or less. The specific surface area of the inorganic substance 2 can be calculated by analyzing measurement results of nitrogen gas adsorption by BET method.

When the specific surface area of the inorganic substance 2 is within the above-described range, the average pore diameter of the open pores 22 can be set in the above-described range even more reliably, and hardness of the nanocomposite resin 1 can be improved reliably.

The inorganic substance 2 preferably has only the open pores 22 as the air gap, and has no closed pore that is independently present in the skeleton 21 without communicating with outside. Even if the inorganic substance 2 has closed pore, the volume ratio of the closed pore relative to a total of the volume of the open pores 22 and the volume of the closed pore is 50% or less. The inorganic substance 2 has an open-pore percentage of, for example, 50% or more, preferably 90% or more.

(2) Organic Polymer

The organic polymer 3 is closely packed in the open pores 22 so as not to generate vacant space in the open pores 22. The organic polymer 3 is a continuous three-dimensional network, and intertwines with the skeleton 21 of the inorganic substance 2. The organic polymer 3 is a polymer of the ingredient monomer.

The ingredient monomer is not particularly limited, and a known ingredient monomer used for medical materials is used. For the ingredient monomer, for example, a radically polymerizable monomer is used, preferably, a ingredient monomer having an ethylenic unsaturated double bond is used.

For the ingredient monomer having an ethylenic unsaturated double bond, for example, α,β-unsaturated carboxylic acid, aromatic vinyl, (meth)acrylamide, and (meth)acrylate are used.

For the α,β-unsaturated carboxylic acid, for example, acrylic acid, methacrylic acid, α-halogenated acrylic acid, crotonic acid, cinnamic acid, sorbic acid, maleic acid, and itaconic acid are used. For aromatic vinyl, for example, styrene is used. For the (meth)acrylamide, for example, acrylamide and methacrylamide are used.

For (meth)acrylate, for example, a monofunctional (meth)acrylate having one (meth)acryloyl group, difunctional (meth)acrylate having two (meth)acryloyl groups, and a trifunctional (meth)acrylate having three (meth)acryloyl groups are used. The (meth)acrylate includes methacrylate and/or acrylate.

Examples of the monofunctional (meth)acrylate include alkyl mono(meth)acrylate (for example, methyl (meth)acrylate, ethyl (meth)acrylate, butyl (meth)acrylate, isobutyl (meth)acrylate, octyl (meth)acrylate, 2-ethyl hexyl (meth)acrylate, lauryl (meth)acrylate, etc.), aryl mono(meth)acrylate (for example, benzyl (meth)acrylate, etc.), amino group-containing mono(meth)acrylate (for example, 2-(N,N-dimethyl amino) ethyl (meth)acrylate, etc.), halogenated alkyl-containing mono(meth)acrylate (for example, 2,3-dibromopropyl (meth)acrylate, etc.), quaternary ammonium salt group-containing mono(meth)acrylate (for example, (meth)acryloyl oxy dodecyl pyridinium bromide, (meth)acryloyl oxy dodecyl pyridinium chloride, (meth)acryloyl oxy hexa decyl pyridinium chloride, (meth)acryloyl oxy decyl ammonium chloride, etc.), hydroxyl group-containing mono(meth)acrylate (for example, 2-hydroxy ethyl (meth)acrylate, 6-hydroxy hexyl (meth)acrylate, 10-hydroxy decyl (meth)acrylate, propylene glycol mono(meth)acrylate, glycerine mono(meth)acrylate, erythritol mono(meth)acrylate, etc.), carboxy group-containing mono(meth)acrylate (for example, 2-methacryloyl oxy ethyl phthalic acid, 2-methacryloyl oxy propyl phthalic acid, etc.), and phosphoric acid group-containing mono(meth)acrylate (for example, EO modified phosphoric acid mono(meth)acrylate, etc.).

Examples of the difunctional (meth)acrylate include alkylene di (meth) acrylate (for example, ethylene glycol di (meth) acrylate, propylene glycol di (meth) acrylate, butanediol di (meth) acrylate, neopentyl glycol di (meth) acrylate, 1,6-hexanediol di (meth) acrylate, 1,10-decanediol di (meth) acrylate, triethylene glycol di (meth) acrylate, etc.), aromatic ring-containing di (meth) acrylate (for example, ethoxy-formed bisphenol A di (meth) acrylate, bisphenol A diglycidyl (meth)acrylate (2,2-bis [4-[3-(meth)acryloyl oxy-2-hydroxy propoxy]phenyl]propane), 2,2-bis [4-(meth)acryloyl oxy ethoxy phenyl]propane, etc.), urethane dimethacrylate (for example, [2,2,4-tri methyl hexa methylene bis(2-carbamoyl oxy ethyl)] dimethacrylate, etc.), hydroxyl group-containing di (meth) acrylate (for example, 1,2-bis [3-(meth)acryloyl oxy-2-hydroxy propoxy]ethane, penta erythritol di (meth) acrylate, glycerine di (meth) acrylate, etc.), phosphoric acid group-containing di (meth) acrylate (for example, EO modified phosphoric acid di (meth) acrylate, etc.), phosphoric acid ester-containing di (meth) acrylate (for example, bis(2-(meth)acryloyl oxy ethyl) phosphoric acid ester, etc.).

For the trifunctional (meth)acrylate, for example, trimethylolpropane tri (meth)acrylate, tri methylol ethane tri (meth)acrylate, and tetra methylol methane tri (meth)acrylate are used.

Of these ingredient monomers having an ethylenic unsaturated double bond, preferably, (meth)acrylates are used, even more preferably, monofunctional (meth)acrylates are used, particularly preferably, alkyl mono(meth)acrylates are used, and most preferably, methyl (meth)acrylates are used.

These ingredient monomers can be used singly, or can be used in combination of two or more.

The ingredient monomer has a viscosity at 25° C. of, for example, 0.1 cP or more, for example, 40,000 cP or less, preferably 15,000 cP or less. The viscosity can be measured by type E viscometer.

(3) Nanocomposite Resin

The nanocomposite resin 1 has a suitable hardness as prosthetics.

The nanocomposite resin 1 has a Vickers hardness of, for example, 100 HV or more, preferably 200 HV or more, and for example, 800 HV or less, preferably 650 HV or less, more preferably 600 HV or less. The Vickers hardness can be measured in accordance with the Vickers hardness test of JIS Z 2244: 2009.

The Vickers hardness of the nanocomposite resin 1 is preferably about the same as the Vickers hardness of the tooth enamel. The Vickers hardness of the tooth enamel changes in accordance with the age of the patient and the parts of the tooth, but for example, it is 100 HV or more and 600 HV or less. The nanocomposite resin 1 has a Vickers hardness in the range of, preferably, ±50 HV of the Vickers hardness of enamel.

The nanocomposite resin 1 has a density of, for example, 1.70 g/cm$^3$ or more, preferably 1.76 g/cm$^3$ or more, and for example, 2.20 g/cm$^3$ or less, preferably less than 2.20 g/cm$^3$, and more preferably 2.00 g/cm$^3$ or less. The density of the nanocomposite resin 1 can be measured by a dry automatic density meter, AccuPyc II 1340.

<Method for Producing Inorganic-Organic Composite Medical Material>

Next, with reference to FIG. 2A to FIG. 2D, description is given below of the method for producing a nanocomposite resin 1 as an embodiment of the method for producing an inorganic-organic composite medical material of the present invention.

Figure 2A:
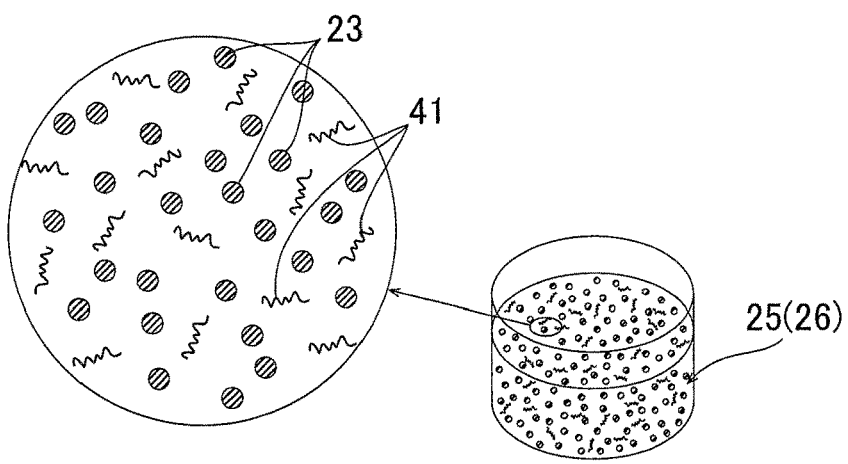
FIG. 2A illustrates the method for producing nanocomposite resin shown in FIG. 1, showing the step of dispersing inorganic nanoparticles in a dispersion medium.
Figure 2B:
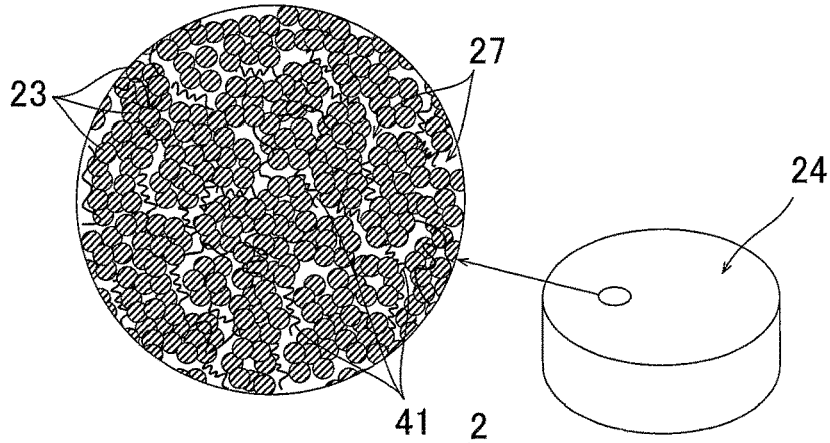
FIG. 2B shows, following FIG. 2A, the step of drying the dispersion medium to form a porous precursor.
Figure 2C:
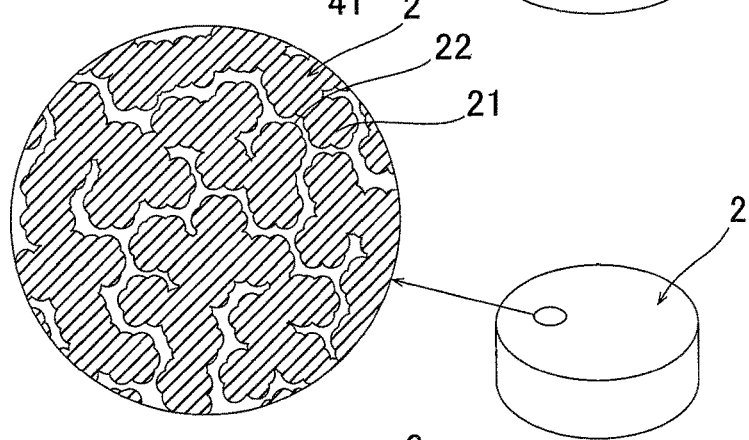
FIG. 2C shows, following FIG. 2B, a step of calcining the porous precursor to form an inorganic calcined substance.
Figure 2D:
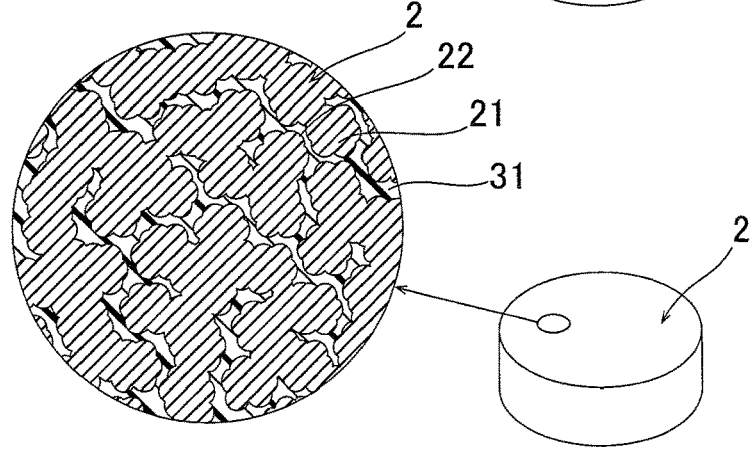
FIG. 2D shows, following FIG. 2C, a step of introducing an ingredient monomer into the open pores of the inorganic calcined substance.

The method for producing the nanocomposite resin 1 includes dispersing inorganic nanoparticles 23 in a dispersion medium (ref: FIG. 2A), drying the dispersion medium to form a porous precursor 24 (ref: FIG. 2B), calcining the porous precursor 24 to form an inorganic substance 2 (ref: FIG. 2C), and filling the open pores 22 of the inorganic substance 2 with the organic polymer 3 (ref: FIG. 1 and FIG. 2D), in sequence.

(1) Inorganic Particle Dispersion Liquid Preparation Step

As shown in FIG. 2A, in the method for producing the nanocomposite resin 1, first, the inorganic nanoparticles 23 are dispersed in the dispersion medium to prepare an inorganic particle dispersion liquid 25.

The inorganic nanoparticles 23 are an ingredient of the inorganic substance 2, and are particles formed from the above-described materials for the inorganic substance 2. For the inorganic nanoparticles 23, preferably, non-metal material particles, even more preferably, metal oxide particles, particularly preferably, silica particles are used.

The inorganic nanoparticles 23 have a nano-order primary particle size. To be specific, the primary particle size range (particle size distribution) of the inorganic nanoparticles 23 is, for example, 0.5 nm or more, preferably 1 nm or more, for example, less than 100 nm, preferably 50 nm or less, more preferably 30 nm or less. The primary particle size of the inorganic nanoparticles 23 can be measured by a transmission electron microscope (TEM).

The inorganic nanoparticles 23 have an average primary particle size of, for example, 1 nm or more, preferably 5 nm or more, and for example, 50 nm or less, preferably 30 nm or less, more preferably 10 nm or less. The average primary particle size of the inorganic nanoparticles 23 can be measured by microsorting control method using a known laser particle size measurement device.

When the inorganic nanoparticles 23 have an average primary particle size of within the above-described range, the average pore diameter range of the open pores 22 can be reliably set within the above-described range. Particularly, when the average primary particle size of the inorganic nanoparticles 23 is more than the above-described upper limit, the average pore diameter of the open pores 22 is more than the above-described upper limit, and hardness of the nanocomposite resin 1 cannot be improved.

The dispersion medium is not particularly limited as long as the inorganic nanoparticles 23 can be dispersed. For the dispersion medium, for example, water and organic solvents (for example, alcohols such as methanol, esters such as ethyl acetate, ketones such as acetone, etc.) are used, and preferably, water is used. The dispersion medium can be used singly, or can be used in combination of two or more.

The inorganic nanoparticles 23 can be dispersed in the dispersion medium without particular limitation, and for example, ultrasonic dispersion, and dispersion with a stirrer are used, and in view of suppressing of coagulation of the inorganic nanoparticles 23, preferably, ultrasonic dispersion is used.

The inorganic nanoparticles 23 can be homogenously dispersed in the dispersion medium without coagulation in this manner, and the inorganic particle dispersion liquid 25 is prepared.

The inorganic particle dispersion liquid has an inorganic nanoparticle content of, for example, 1 mass % or more, preferably 5 mass % or more, and for example, 50 mass % or less, preferably 20 mass % or less.

To the inorganic particle dispersion liquid 25, a water-soluble polymer 41 is blended preferably along with the inorganic nanoparticles 23. When the inorganic particle dispersion liquid 25 is blended with the water-soluble polymer 41, the nanopores 27 can be reliably formed in the porous precursor 24 to be described later.

Examples of the water-soluble polymer 41 include vinyl polymers (for example, polyvinyl alcohol, polyvinyl pyrrolidone, etc.), polysaccharide polymers (for example, cellulose, chitin, chitosan, starch, dialdehyde starch, dextrin, carrageenan, sodium alginate, xanthan gum, pullulan, agar, etc.), amino acid polymer (for example, casein, gelatin, collagen, albumen, plant-derived viscous material, etc.), polyester polymer (for example, polylactic acid, etc.), acrylic polymer (for example, sodium polyacrylate, poly methyl methacrylate, etc.), amide polymer (for example, poly acrylamide, etc.), and ether polymer (for example, polyethylene oxide, etc.). The water-soluble polymer 41 can be used singly, or can be used in combination of two or more.

Of these examples of the water-soluble polymer 41, preferably, vinyl polymer is used, even more preferably, poly vinyl alcohol is used.

The water-soluble polymer 41 has a number average molecular weight of, for example, 40,000 or more, preferably 80,000 or more, and for example, 300,000 or less, preferably 200,000 or less.

To blend the water-soluble polymer 41 in the inorganic particle dispersion liquid 25, for example, a water-soluble polymer solution in which the water-soluble polymer 41 is dissolved in the above-described dispersion medium in advance is prepared, and the water-soluble polymer solution is added to the inorganic particle dispersion liquid 25.

The dispersion medium for the water-soluble polymer solution is preferably the same as the dispersion medium for the inorganic particle dispersion liquid 25. The water-soluble polymer solution has a water-soluble polymer 41 content of, for example, 1 mass % or more, preferably 5 mass % or more, and for example, 50 mass % or less, preferably 20 mass % or less.

The water-soluble polymer solution is added in an amount of, relative to 100 parts by mass of the inorganic particles dispersion liquid, for example, 1 part by mass or more, preferably 10 parts by mass or more, and for example, 50 parts by mass or less, preferably 30 parts by mass or less.

The inorganic particle dispersion liquid 25 to which the water-soluble polymer solution was added is mixed so that the inorganic nanoparticles 23 and the water-soluble polymer 41 are homogenous.

In this manner, the inorganic particle dispersion liquid 25 in which the water-soluble polymer 41 is blended (hereinafter referred to as polymer-blended dispersion liquid 26) is prepared. In the polymer-blended dispersion liquid 26, the inorganic nanoparticles 23 are dispersed in the dispersion medium, and the water-soluble polymer 41 is dissolved in the dispersion medium.

The range of the inorganic nanoparticles 23 content in the polymer-blended dispersion liquid 26 is, for example, the same as the range of the inorganic nanoparticles 23 content in the above-described inorganic particle dispersion liquid 25. The polymer-blended dispersion liquid 26 has a water-soluble polymer 41 content of, for example, 0.1 mass % or more, preferably 1 mass % or more, and for example, 20 mass % or less, preferably 5 mass % or less.

The water-soluble polymer 41 content relative to 1 part by mass of the inorganic nanoparticle is, for example, 0.02 parts by mass or more, preferably 0.1 parts by mass or more, and for example, 0.45 parts by mass or less, preferably 0.3 parts by mass or less.

As necessary, the pH of the polymer-blended dispersion liquid 26 is adjusted to be in the range of 2.0 to 4.0. When the pH of the polymer-blended dispersion liquid 26 is adjusted to be in the above-described range, the nanopores 27 can be formed even more stably in the porous precursor 24 to be described later.

To adjust the pH of the polymer-blended dispersion liquid 26, for example, acid (for example, sulfuric acid, nitric acid, etc.) is added to the inorganic particle dispersion liquid 25 to adjust the pH of the inorganic particle dispersion liquid 25, and then the water-soluble polymer solution is added to the inorganic particle dispersion liquid 25. It is also possible to mix the inorganic particle dispersion liquid 25 with the water-soluble polymer solution, and then acid is added to adjust the pH of the polymer-blended dispersion liquid 26.

In this embodiment, the water-soluble polymer solution is added to the inorganic particle dispersion liquid 25 to prepare the polymer-blended dispersion liquid 26, but it is not limited thereto, and the water-soluble polymer 41 can be directly blended to the inorganic particle dispersion liquid 25.

(2) Preparation Step of Porous Precursor

Then, as shown in FIG. 2B, the inorganic particle dispersion liquid 25 (preferably, polymer-blended dispersion liquid 26) is dried to form the porous precursor 24 having the nanopores 27. In this embodiment, the case where the polymer-blended dispersion liquid 26 is dried is described.

The drying temperature of the polymer-blended dispersion liquid 26 is not particularly limited as long as the dispersion medium can be removed, and for example, 10° C. or more, preferably 20° C. or more, and for example, 50° C. or less, preferably 40° C. or less.

Then, the polymer-blended dispersion liquid 26 is dried until the inorganic nanoparticles 23 content of the porous precursor 24 is in the range to be described later, to remove the dispersion medium.

In this manner, a gelled porous precursor 24 is formed from the inorganic nanoparticles 23 and the water-soluble polymer 41. In the porous precursor 24, water-soluble polymer 41 enters between the dispersed inorganic nanoparticles 23 and the nanopores 27 derived from the water-soluble polymer 41 is formed.

The inorganic nanoparticles 23 content of the porous precursor 24 is, for example, 50 mass % or more, preferably 70 mass % or more, and for example, 99 mass % or less, preferably 95 mass % or less.

The nanopores 27 has an average pore diameter of, when the average pore diameter of the open pore 22 is set to 100%, for example, 10% or more, preferably 50% or more, and for example, 300% or less, preferably 200% or less. To be specific, the nanopores 27 have an average pore diameter of, for example, 0.1 nm or more, preferably 1 nm or more, more preferably 5 nm or more, and for example, 300 nm or less, preferably 100 nm or less. The average pore diameter of the nanopores 27 can be calculated by analyzing the measurement result of nitrogen gas adsorption by BJH method.

In this embodiment, the polymer-blended dispersion liquid 26 is dried to form the porous precursor 24, but it is not limited thereto, and the inorganic particle dispersion liquid 25 containing no water-soluble polymer 41 can be dried in the same manner as described above to form the porous precursor 24. In this case, the porous precursor 24 is formed from the inorganic nanoparticles 23.

(3) Preparation Step of Inorganic Substance

Next, as shown in FIG. 2C, the porous precursor 24 is calcined, for example, in air to form the inorganic substance 2 as the inorganic calcined substance.

The nanopores 27 of the porous precursor 24 become smaller as it is calcined, and are closed when it is completely calcined. Therefore, the calcination conditions of the porous precursor 24 are milder than the conditions for, for example, the inorganic substance 2 (inorganic calcined substance) to be a compact inorganic substance 2 having no open pore 22. With such mild calcination conditions, the average pore diameter of the open pores 22 of the inorganic substance 2 can be adjusted to be in the above-described range.

The milder calcination conditions are the conditions that allow the pore diameter of the nanopores 27 to be 99% to 1% when the pore diameter of the nanopores 27 of the porous precursor 24 is set to 100% and when they are closed is set to 0%. For example, when the calcining temperature is constant, the calcining time is, setting the time when the nanopores 27 close from the start of calcinations as 100%, for example, 1% or more, preferably 10% or more, and for example, 99% or less, preferably 90% or less.

To be specific, the calcining temperature of the porous precursor 24 is, for example, 600° C. or more, preferably 1000° C. or more, more preferably 1050° C. or more, and for example, 1700° C. or less, preferably 1200° C. or less. The calcining time for the porous precursor 24 is, for example, 1 hour or more, preferably 2 hours or more, more preferably 3 hours or more, particularly preferably 4 hours or more, for example, 15 hours or less, preferably 6 hours or less.

The porous precursor 24 can be calcined only once under the above-described conditions, or can be calcined a plurality of times. For example, when the porous precursor 24 is calcined twice, primary calcination is done at 600° C. or more and 950° C. or less, and then secondary calcination is done at, for example, 1050° C. or more and 1200° C. or less.

In this manner, when the porous precursor 24 contains the water-soluble polymer 41, the plurality of inorganic nanoparticles 23 are sintered each other by calcination along with the volatilization and burning of the water-soluble polymer 41, thereby preparing the inorganic substance 2 (sintered inorganic substance) having open pores 22 with the average pore diameter in the above-described range and a specific surface area of the above-described upper limit or less.

(4) Organic Polymer Filling

Next, the open pores 22 of the inorganic substance 2 are filled with the organic polymer 3.

To fill the open pores 22 with the organic polymer 3, for example, as shown in FIG. 2D, the ingredient monomer 31 of the organic polymer 3 is introduced into the open pores 22, and then the ingredient monomer 31 introduced in the open pores 22 is polymerized to form the organic polymer 3.

For the ingredient monomer 31, for example, the above-described ingredient monomer is used, and preferably, the above-described ingredient monomer having an ethylenic unsaturated double bond is used. To the ingredient monomer 31, as necessary, a polymerization initiator is added.

For the polymerization initiator, for example, a known polymerization initiator used for medical materials is used, and preferably, organic peroxide (for example, benzoyl peroxide, cumene hydroperoxide, etc.) is used. The polymerization initiator can be used singly, or can be used in combination of two or more. The polymerization initiator is added in an amount relative to 100 parts by mass of the ingredient monomer of, for example, 0.1 parts by mass or more and 20 parts by mass or less.

To introduce the ingredient monomer 31 to the open pores 22, for example, the inorganic substance 2 is immersed in the ingredient monomer 31.

The immersion pressure is, for example, 10 kPa or more, preferably 50 kPa or more, and for example, 10,000 kPa or less, preferably 1,000 kPa or less, even more preferably, atmospheric pressure (101 kPa).

The immersion temperature is, for example, 1° C. or more, preferably 10° C. or more, and for example, 50° C. or less, preferably 30° C. or less, even more preferably, room temperature (25° C.).

The immersion time is, for example, 1 hour or more, preferably 10 hours or more, for example, 50 hours or less, preferably 30 hours or less.

In this manner, the ingredient monomer 31 is introduced into the open pores 22.

Then, to polymerize the ingredient monomer 31 introduced into the open pores 22, for example, the ingredient monomer 31 is heated.

The heating temperature is, for example, 40° C. or more, preferably 50° C. or more, and for example, 100° C. or less, preferably 70° C. or less.

The heating time is, for example, 1 hour or more, preferably 40 hours or more, and for example, 100 hours or less, preferably 60 hours or less.

In this manner, the ingredient monomer 31 is polymerized to form the organic polymer 3.

In this embodiment, the ingredient monomer is heated to polymerize, but it is not limited thereto, and the ingredient monomer can be polymerized by application of visible light or ultraviolet light without heating, or polymerized by heating and application of light. In this embodiment, the ingredient monomer is a radically polymerizable monomer, but it is not limited thereto, and the ingredient monomer can be a condensation monomer. For example, condensation monomers of poly carboxylic acid and polyol can be introduced into the open pores, and then polymerized.

In this embodiment, the ingredient monomer is introduced into the open pore, and then the ingredient monomer is polymerized to form the organic polymer, but it is not limited thereto, and the organic polymer can be introduced into the open pore.

As described above, as shown in FIG. 1, the open pores 22 of the inorganic substance 2 are filled with the organic polymer 3, thereby producing the nanocomposite resin 1 having the two-phase co-continuous structure of the inorganic substance 2 with the open pores 22 and the organic polymer 3 filling the open pores 22.

<Use of Nanocomposite Resin>

Such a nanocomposite resin 1 can be suitably used as a prosthetic in various medical fields. The nanocomposite resin 1 can be used for, for example, medical use artificial bone, bone substitute, dental material, and medical educational material, and preferably, dental material (inorganic-organic composite dental material), even more preferably, a CAD/CAM dental restoration material.

<Operations and Effects>

As shown in FIG. 1, in the nanocomposite resin 1, the open pores 22 have an average pore diameter of the above-described lower limit or more. Therefore, the open pores 22 of the inorganic substance 2 can be filled sufficiently with the organic polymer 3, and the two-phase co-continuous structure of the inorganic substance 2 and the organic polymer 3 can be ensured. As a result, the nanocomposite resin 1 can be suppressed from being brittle.

In the nanocomposite resin 1, the open pores 22 have an average pore diameter of the above-described upper limit or less, and the inorganic substance 2 has a specific surface area of the above-described upper limit or less. Therefore, hardness of the nanocomposite resin 1 can be improved.

As a result, hardness of the nanocomposite resin 1 can be set to a suitable hardness as prosthetics, particularly, about the hardness of enamel.

The inorganic substance 2 is preferably, metal oxide. Therefore, hardness of the nanocomposite resin 1 can be reliably improved to a suitable hardness as prosthetics, particularly, about the hardness of enamel.

The organic polymer 3 is preferably a polymer of an ingredient monomer having an ethylenic unsaturated double bond. Therefore, the open pores 22 can be reliably filled with the organic polymer 3, and the two-phase co-continuous structure of the inorganic substance 2 and the organic polymer 3 can be stably ensured.

In the method for producing the nanocomposite resin 1, as shown in FIG. 2A to FIG. 2D, the inorganic nanoparticles 23 are dispersed in the dispersion medium, and then the dispersion medium is dried to form the porous precursor 24 having the nanopores 27, and then the porous precursor 24 is calcined to form the inorganic substance 2 having the open pores 22 of the average pore diameter of the above-described nano-order range and the specific surface area of the above-described upper limit or less, and then the open pores 22 of the inorganic substance 2 are filled with the organic polymer 3. The nanocomposite resin 1 having a suitable hardness as prosthetics can be produced in this manner.

As shown in FIG. 2C, with the above-described method, the porous precursor 24 is calcined to form the inorganic calcined substance having the open pores 22, and therefore by suitably changing the calcination conditions, the average pore diameter of the open pores 22 can be adjusted within the above-described nano-order range, and the specific surface area can be adjusted to the above-described upper limit or less.

Therefore, with an easy method, by adjusting the average pore diameter of the open pores 22 within the above-described range, and adjusting the specific surface area to the above-described upper limit or less, the Vickers hardness of the nanocomposite resin 1 can be freely adjusted to the above-described range, and a nanocomposite resin 1 with a desired hardness can be efficiently produced.

As shown in FIG. 2A and FIG. 2B, to the inorganic particle dispersion liquid 25, preferably, the water-soluble polymer 41 is blended along with the inorganic nanoparticles 23. Then, by drying the polymer-blended dispersion liquid 26 to which the inorganic nanoparticles 23 and the water-soluble polymer 41 are blended, the porous precursor 24 is formed. Therefore, in the porous precursor 24, the nanopores 27 derived from the water-soluble polymer 41 can be reliably formed.

Then, by calcining the porous precursor 24 having the nanopores 27, the inorganic substance 2 is formed, and therefore the open pores 22 having the average pore diameter of the above-described nano-order range can be reliably formed.

As shown in FIG. 2C, the porous precursor 24 is calcined under milder conditions where the inorganic substance 2 becomes the compact inorganic calcined substance having no open pores 22. Therefore, the open pores 22 can be reliably formed in the inorganic substance 2.

The porous precursor 24 is calcined under milder conditions to adjust the average pore diameter of the open pores 22 to the above-described nano-order range. Therefore, hardness of the nanocomposite resin 1 can be reliably adjusted.

In this embodiment, as shown in FIG. 2D, after introducing the ingredient monomer 31 of the organic polymer 3 in the open pores 22, the ingredient monomer 31 is polymerized to form the organic polymer 3. Therefore, compared with the case where the polymerized organic polymer 3 is introduced into the open pores 22, the ingredient monomer 31 can be introduced into the open pores 22 smoothly, and the open pores 22 can be reliably filled with the organic polymer 3.

EXAMPLES

The present invention is further described in detail based on EXAMPLES below. However, the present invention is not limited to Examples. The specific numeral values such as mixing ratio (content), physical property values, and parameters used in the description below can be replaced with the upper limit value (numeral values defined with "or less", "less than") or the lower limit value (numeral values defined with "or more", "more than") of the corresponding mixing ratio (content), physical property values, parameters in the above-described "DESCRIPTION OF EMBODIMENTS".

1. Preparation of Sintered Silica Glass

Examples 1 to 4 and Comparative Examples 1 and 2

Silica particles having an average primary particle size of 7 nm (inorganic nanoparticles, fumed silica, trade name: Aerosil300, manufactured by NIPPON AEROSIL CO., LTD.) were dispersed by ultrasonic dispersion in distillation water (dispersion medium).

In this manner, silica particle dispersion liquid with a silica particle content of 10 mass % (inorganic particles dispersion liquid) was prepared. Thereafter, nitric acid was added in a suitable amount to the silica particle dispersion liquid to adjust the pH of the silica particle dispersion liquid to 3.

Poly vinyl alcohol (PVA, water-soluble polymer, number average molecular weight 129,000) was dissolved in distillation water (dispersion medium).

In this manner, a PVA aqueous solution (water-soluble polymer solution) with a PVA content of 10 mass % was prepared.

Then, 11.4 g of the PVA aqueous solution was added to 60 g of the silica particle dispersion liquid, and the mixture was stirred at 25° C. (room temperature) so that silica particles and PVA were homogenous.

In this manner, silica particles were dispersed, and a PVA-blended dispersion liquid (polymer-blended dispersion liquid) in which PVA was dissolved was prepared. In the PVA-blended dispersion liquid, the silica particle content was 8.4 mass %, and the PVA content was 1.6 mass %. The PVA content relative to 1 part by mass of silica particles was 0.19 parts by mass.

Then, the PVA-blended dispersion liquid was disposed in a fluorine resin vessel, and dried at 30° C. for 168 hours.

In this manner, a gelled porous precursor was prepared from silica particles and PVA. The porous precursor had a silica particle content of 84 mass %.

Then, the porous precursor was calcined in air at 1130° C. for the time shown in Table 1.

In this manner, PVA was volatilized and burned, and the plurality of silica particles were bonded to each other to prepare sintered silica glass having open pores (inorganic substance).

Comparative Example 3

Sintered silica glass having open pores (inorganic substance) was prepared in the same manner as in Example 2, except that the silica particles having an average primary particle size of 7 nm was changed to silica particles having an average primary particle size of 200 nm.

(Evaluation on Sintered Silica Glass)

Figure 3A:
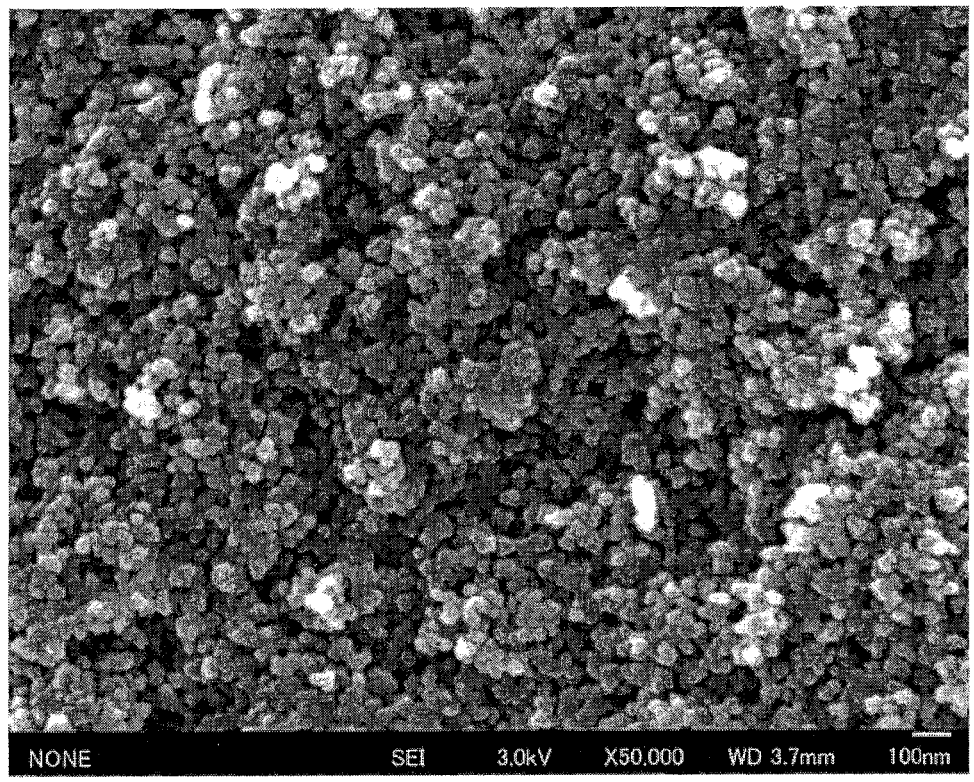
FIG. 3A shows an FE-SEM image of a sintered silica glass of Example 1.
Figure 3B:
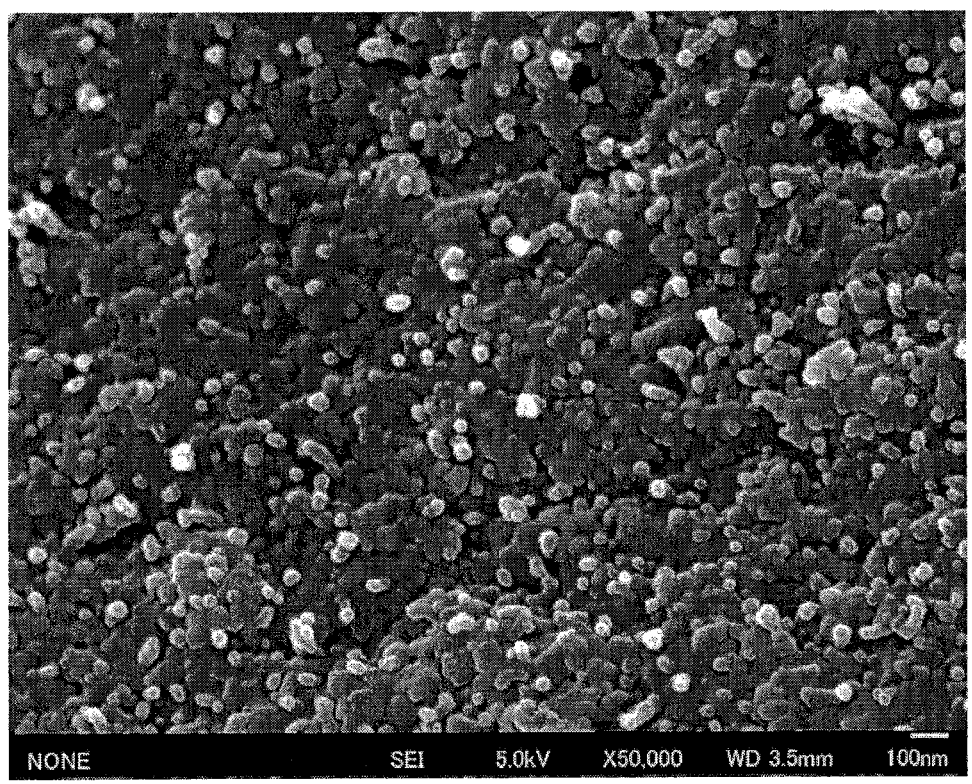
FIG. 3B shows an FE-SEM image of the sintered silica glass of Example 3.

The sintered silica glass (calcining time: 3 hours) of Example 1 and sintered silica glass (calcining time: 5 hours) of Example 3 were photographed by FE-SEM (Field Emission-Scanning Electron Microscope). FIG. 3A shows an FE-SEM image of the sintered silica glass of Example 1, and FIG. 3B shows an FE-SEM image of the sintered silica glass of Example 3. FIG. 3A and FIG. 3B confirmed that the sintered silica glass had open pores formed therein.

Figure 4:
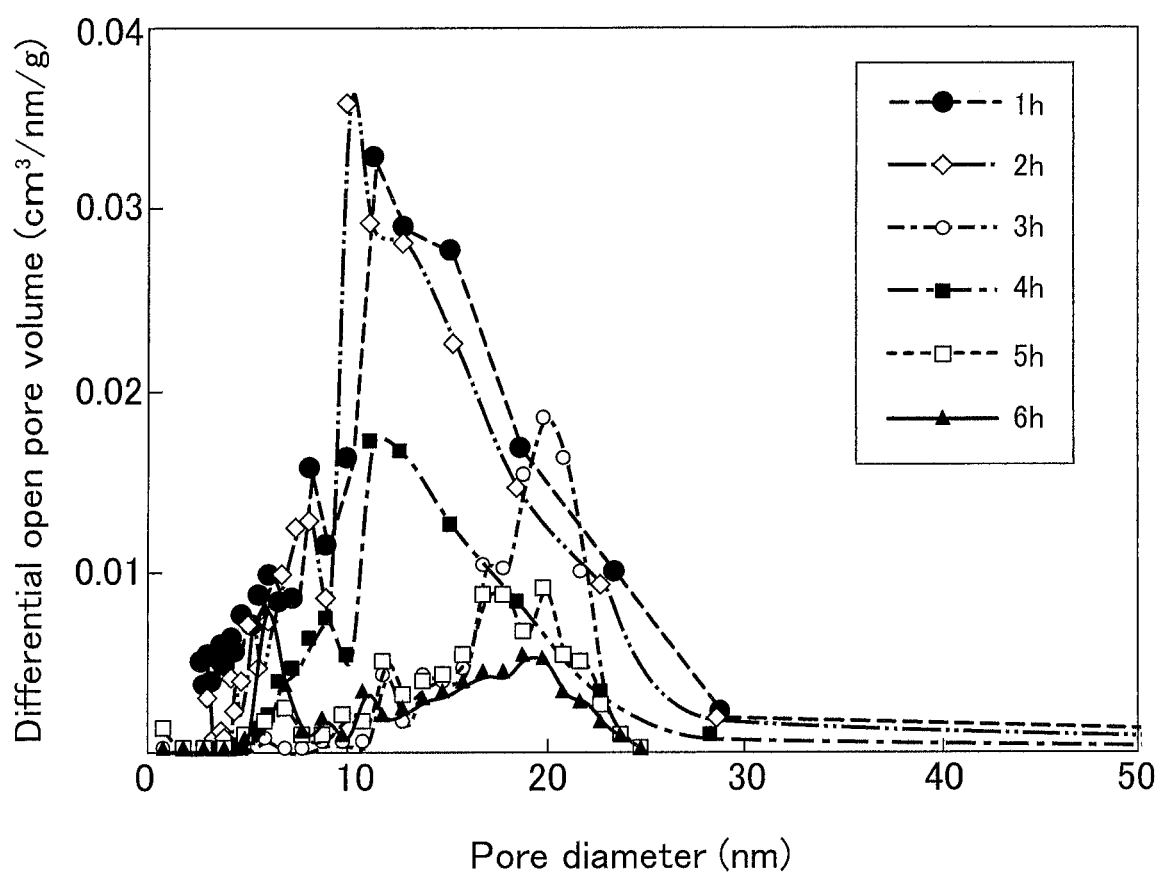
FIG. 4 shows pore size distribution of open pores in the sintered silica glass of Examples and Comparative Examples.

The pore size distribution of the open pores of the sintered silica glass of Examples and Comparative Examples was measured by nitrogen gas adsorption method with QuadraSorb SI (manufactured by Quantachrome Instruments), and the measurement result was analyzed by BJH method. The results of Examples 1 to 4 and Comparative Examples 1 and 2 are shown in FIG. 4.

The average pore diameter of the open pore was calculated based on the pore size distribution of Examples and Comparative Examples. The results are shown in Table 1.

Figure 5:
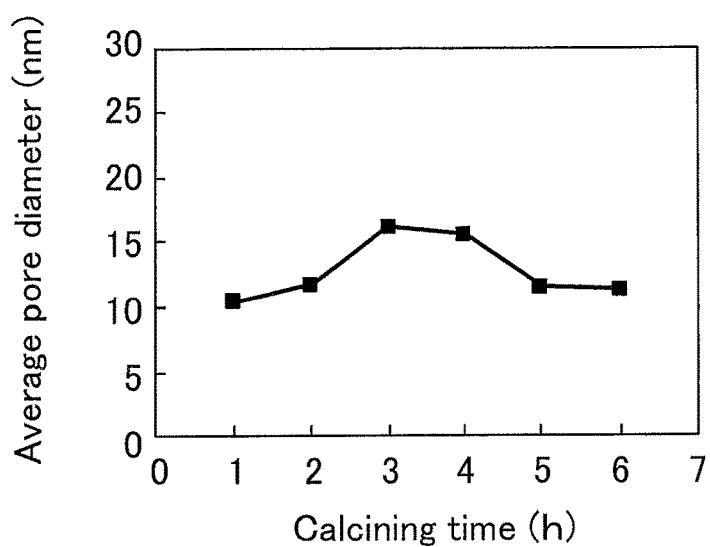
FIG. 5 is a graph illustrating correlation between calcining time and the average pore diameter of the open pore of the sintered silica glass of Examples and Comparative Examples.

Upper limit of the average pore diameter of the open pores that can be calculated from the measurement result by the nitrogen gas adsorption is 100 nm or less, and when the average pore diameter of the open pore is more than 100 nm, the measurement and calculation based on nitrogen gas adsorption cannot be conducted. The average pore diameter of the open pore of the sintered silica glass in Comparative Example 3 could not be measured or calculated based on the nitrogen gas adsorption method, and it is assumed to be more than 100 nm. FIG. 5 shows correlation between the calcining time and the average pore diameter of the open pores in Examples 1 to 4 and Comparative Examples 1 and 2.

Figure 6:
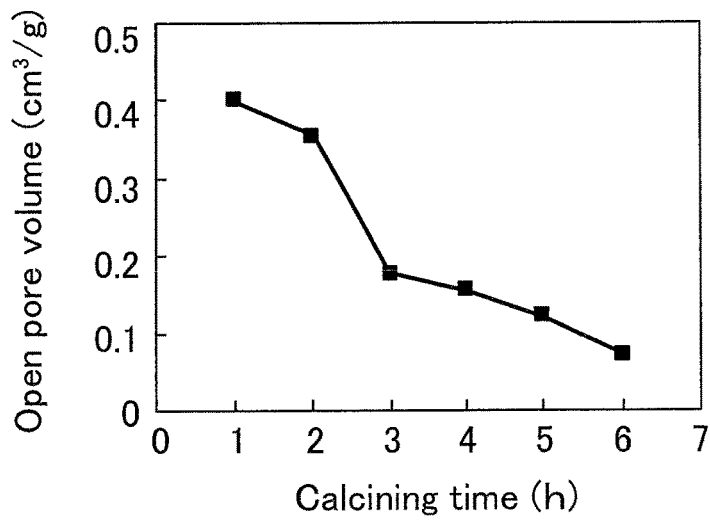
FIG. 6 is a graph illustrating correlation between calcining time and the volume of the open pores of the sintered silica glass of Examples and Comparative Examples.

The volume of the open pore was calculated based on the pore size distribution of Examples and Comparative Examples. The results are shown in Table 1. FIG. 6 shows correlation between the calcining time and the volume of the open pore in Examples 1 to 4 and Comparative Examples 1 and 2.

Figure 7:
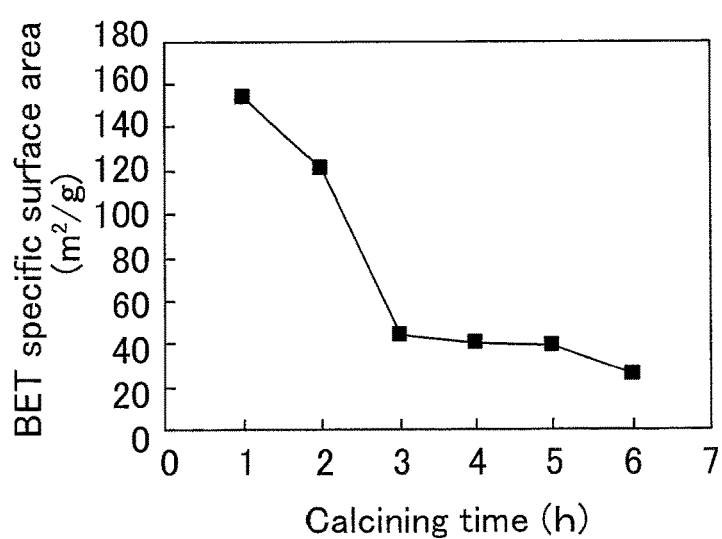
FIG. 7 is a graph illustrating correlation between calcining time and the specific surface area of the sintered silica glass of Examples and Comparative Examples.

The specific surface area of the sintered silica glass of Examples and Comparative Examples was measured based on nitrogen gas adsorption with QuadraSorb SI (manufactured by Quantachrome Instruments), and the measurement result was analyzed by BET method. The results are shown in Table 1. FIG. 7 shows correlation between the calcining time and specific surface area of Examples 1 to 4 and Comparative Examples 1 and 2.

2. Filling Open Pores with Poly Methyl Methacrylate 10 g of methyl methacrylate (MMA, ingredient monomer) was prepared, and 0.05 g of benzoyl peroxide (BPO, polymerization initiator) was dissolved in the MMA.

Then, the porous precursor of Examples and Comparative Examples was immersed in the MMA in which BPO was dissolved under 101 kPa (atmospheric pressure) at 25° C. (room temperature) for 24 hours.

In this manner, the MMA was introduced in the open pores of the porous precursor.

Thereafter, the porous precursor to which MMA was introduced was heated to 60° C., and kept for 48 hours.

In this manner, the MMA was polymerized, and poly methyl methacrylate (PMMA, organic polymer) was formed.

The nanocomposite resin having the two-phase co-continuous structure of the sintered silica glass having open pores and PMMA filling the open pores was produced in the above-described manner. The density of the nanocomposite resin of Examples and Comparative Examples was measured. The results are shown in Table 1.

Figure 8:
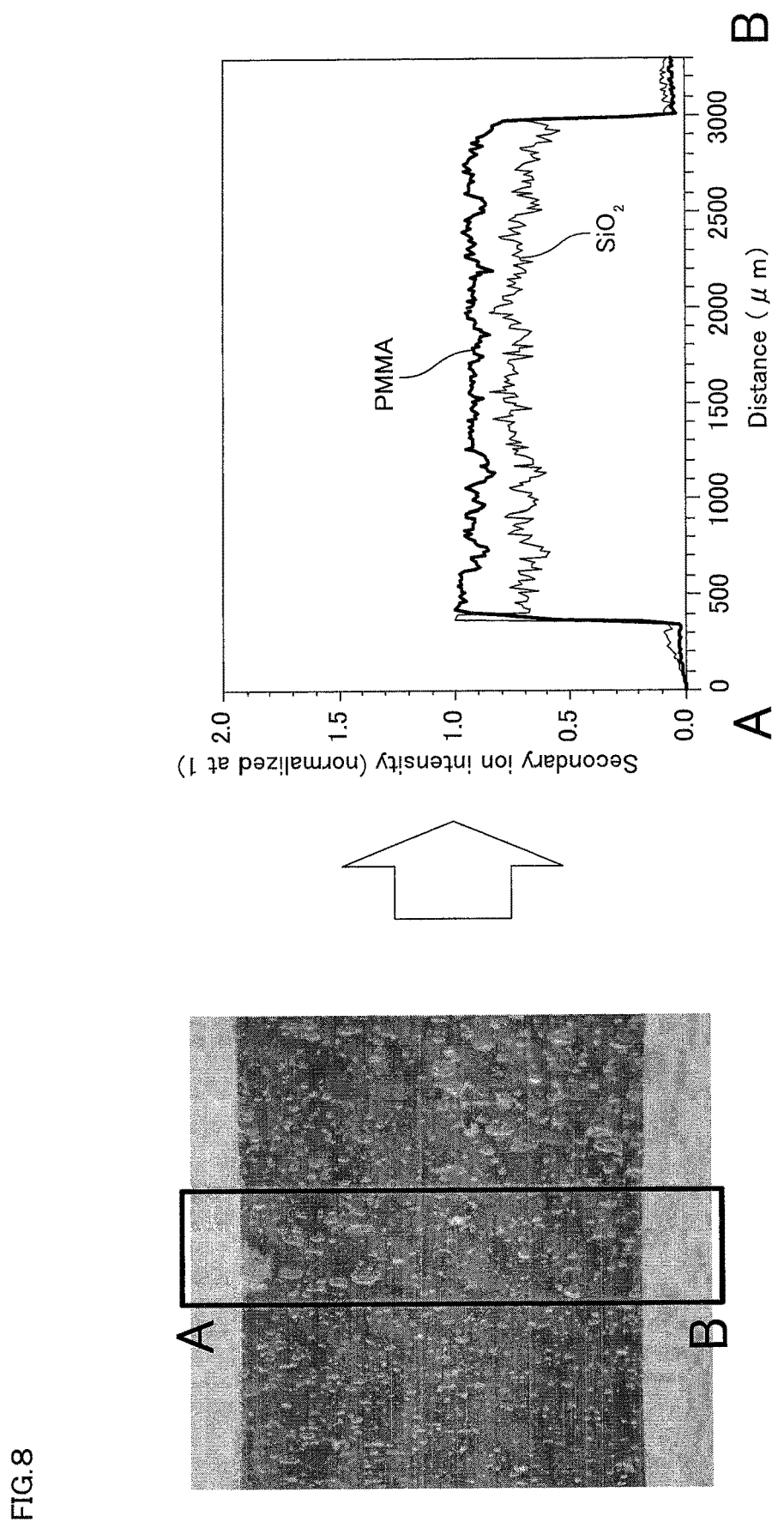
FIG. 8 shows TOF-SIMS spectrum of the nanocomposite resin of Example 1.

The nanocomposite resin of Example 1 was analyzed by Time-of-Flight Secondary Ion Mass Spectrometry (TOF-SIMS). The results are shown in FIG. 8. The left side portion of the FIG. 8 shows the region of the nanocomposite resin subjected to TOF-SIMS analysis. FIG. 8 confirmed that in the entire range subjected to the analysis, the PMMA secondary ion intensity was constant and the PMMA filling was homogenous throughout the nanocomposite resin.

Figure 9:
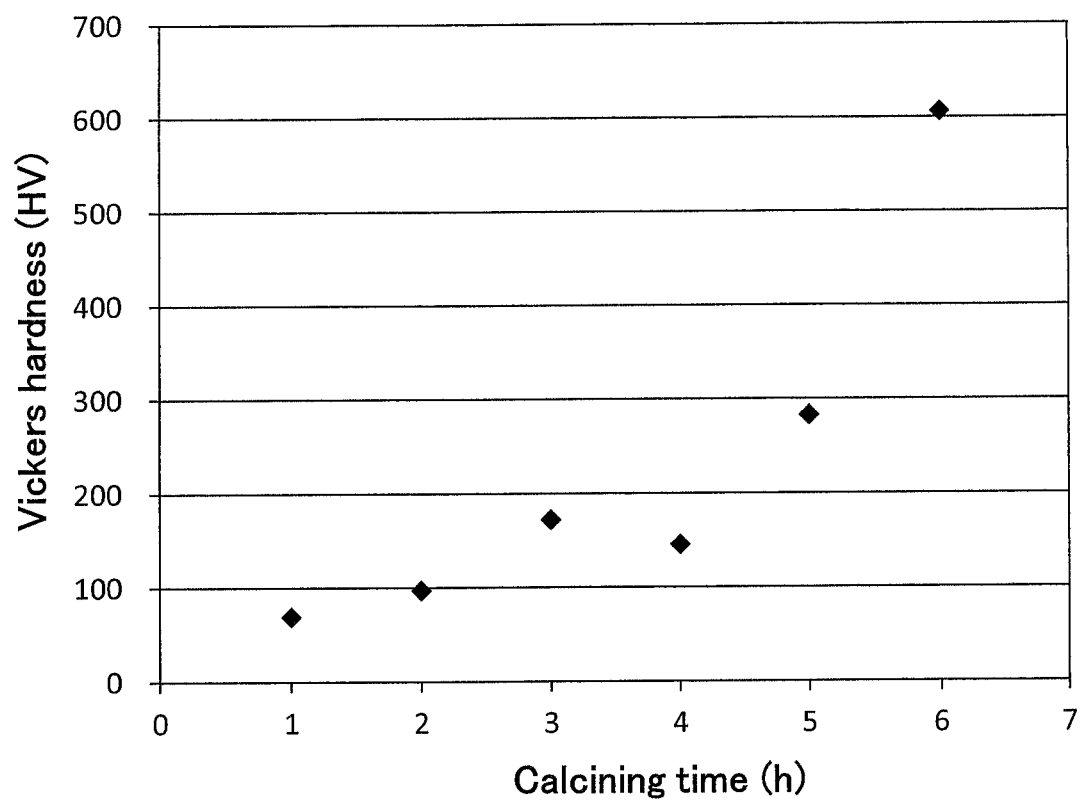
FIG. 9 is a graph illustrating correlation between calcining time and Vickers hardness of the nanocomposite resin of Examples and Comparative Examples.

The Vickers hardness of the nanocomposite resin of Examples and Comparative Examples was measured in accordance with JIS Z 2244: 2009. The results are shown in Table 1. FIG. 9 shows correlation between calcining time and Vickers hardness in Examples 1 to 4 and Comparative Examples 1 and 2.

TABLE 1

| no. | | | Comp. Ex. 1 | Comp. Ex. 2 | Example 1 | Example 2 | Example 3 | Example 4 | Comp. Ex. 3 |
|---|---|---|---|---|---|---|---|---|---|
| Calcining time | | [h] | 1 | 2 | 3 | 4 | 5 | 6 | 4 |
| Silica glass | Average pore diameter of open pore | [nm] | 10.4 | 11.7 | 16.1 | 15.6 | 11.4 | 11.3 | 100< |
| | Specific surface area | [m$^2$/g] | 153.4 | 121.1 | 44.0 | 40.1 | 39.2 | 25.7 | 8.5 |
| | Volume of open pore | [cm$^3$/g] | 0.40 | 0.35 | 0.18 | 0.16 | 0.12 | 0.07 | 0.01 |
| Nanocomposite resin | Density | [g/cm$^3$] | 1.57 | 1.75 | 1.79 | 1.87 | 1.99 | 2.19 | 2.08 |
| | Vickers hardness | [HV] | 69.3 | 97.1 | 172.0 | 145.4 | 283.0 | 606.5 | 32.5 |

While the illustrative embodiments of the present invention are provided in the above description, such is for illustrative purpose only and it is not to be construed as limiting the scope of the present invention. While the illustrative embodiments of the present invention are provided in the above description, such is for illustrative purpose only and it is not to be construed as limiting the scope of the present invention.

INDUSTRIAL APPLICABILITY

The inorganic-organic composite medical material of the present invention can be suitably used for, for example, prosthetics in various medical fields, to be specific, medical artificial bones, bone substitute, dental material, and medical educational material. The method for producing an inorganic-organic composite medical material of the present invention is suitably used, for example, production of an inorganic-organic composite medical material used for prosthetics in various medical fields.

DESCRIPTION OF REFERENCE NUMERALS 1 nanocomposite resin
2 inorganic substance
3 organic polymer
22 open pore
23 inorganic nanoparticles
24 porous precursor
31 ingredient monomer
41 water-soluble polymer

The invention claimed is:
1. An inorganic-organic composite medical material comprising:
a two-phase co-continuous structure of an inorganic substance having open pores and an organic polymer filling the open pores, wherein the inorganic substance includes a skeleton, in which particles of a plurality of metal oxide are bonded together and which is metal oxide glass of a continuous three-dimensional network,
the open pores are a space portion formed in a three-dimensional network and defined by the skeleton,
the open pores have an average pore diameter of 1 nm or more and 100 nm or less, and
the inorganic substance has a specific surface area of 100 $m^2/g$ or less.

2. The inorganic-organic composite medical material according to claim 1, wherein
the organic polymer is a polymer of an ingredient monomer having an ethylenic unsaturated double bond.

3. A method for producing an inorganic-organic composite medical material, the method comprising the steps of:
dispersing inorganic nanoparticles which are particles of metal oxide in a dispersion medium,
drying the dispersion medium to form a porous precursor having nanopores from the inorganic nanoparticles,
calcining the porous precursor to form an inorganic calcined substance having a skeleton, in which the inorganic nanoparticles are bonded together, and open pores, which are a space portion defined by the skeleton, with an average pore diameter of 1 nm or more and 100 nm or less, and having a specific surface area of 100 $m^2/g$ or less, and
filling the open pores of the inorganic calcined substance with an organic polymer, thereby producing an inorganic-organic composite medical material having a two-phase co-continuous structure of the inorganic substance having open pores and the organic polymer filling the open pores.

4. The method for producing an inorganic-organic composite medical material according to claim 3, wherein
in the step of dispersing the inorganic nanoparticles in the dispersion medium,
a water-soluble polymer is blended in the dispersion medium along with the inorganic nanoparticles to disperse the inorganic nanoparticles in the dispersion medium,
in the step of forming the porous precursor,
the dispersion medium is dried to form the porous precursor having nanopores based on the water-soluble polymer from the inorganic nanoparticles and the water-soluble polymer.

5. The method for producing an inorganic-organic composite medical material according to claim 3, wherein
in the step of forming the inorganic calcined substance,
the porous precursor is calcined at a short calcining time shorter than a calcining time where the inorganic calcined substance is formed into a compact inorganic calcined substance having no open pore.

6. The method for producing an inorganic-organic composite medical material according to claim 5, wherein
the average pore diameter of the open pores is adjusted to be in the range of 1 nm or more and 100 nm or less by the short calcining time.

7. The method for producing an inorganic-organic composite medical material according to claim 3, wherein
the step of filling the open pores of the inorganic calcined substance with the organic polymer includes
introducing an ingredient monomer of the organic polymer in the open pores, and
polymerizing the ingredient monomer introduced in the open pores to form the organic polymer.

* * * * *